United States Patent
Benarie

(10) Patent No.: US 7,865,240 B2
(45) Date of Patent: Jan. 4, 2011

(54) IMPLANTABLE PULSE GENERATOR PROGRAMMING VIA ELECTRODES

(75) Inventor: Jacob Benarie, Haifa (IL)

(73) Assignee: Betastim, Ltd., Caesarea (IL)

( * ) Notice: Subject to any disclaimer, the term of this patent is extended or adjusted under 35 U.S.C. 154(b) by 66 days.

(21) Appl. No.: 11/965,997

(22) Filed: Dec. 28, 2007

(65) Prior Publication Data

US 2009/0171410 A1 Jul. 2, 2009

(51) Int. Cl.
*A61N 1/00* (2006.01)
(52) U.S. Cl. .......................................................... 607/9
(58) Field of Classification Search ...................... 607/9, 607/40
See application file for complete search history.

(56) References Cited

U.S. PATENT DOCUMENTS

| | | | |
|---|---|---|---|
| 5,263,480 A | | 11/1993 | Wernicke et al. |
| 5,690,691 A | * | 11/1997 | Chen et al. ................... 607/40 |
| 6,579,301 B1 | | 6/2003 | Bales et al. |
| 2003/0181958 A1 | | 9/2003 | Dobak, III |
| 2004/0176685 A1 | | 9/2004 | Takizawa et al. |
| 2005/0137633 A1 | * | 6/2005 | Salo et al. ...................... 607/9 |

FOREIGN PATENT DOCUMENTS

WO   WO 2005/007232   1/2005

OTHER PUBLICATIONS

Supplementary European Search Report dated Sep. 11, 2009, which issued during the prosecution of Applicant's European Patent Application No. EP 06 76 6139.
An Office Action dated Aug. 19, 2009, which issued during the prosecution of Applicant's U.S. Appl. No. 11/279,355.

* cited by examiner

*Primary Examiner*—George Manuel
*Assistant Examiner*—Shubatra Narayanaswamy
(74) *Attorney, Agent, or Firm*—Stein McEwen, LLP

(57) ABSTRACT

Apparatus is provided, including a control unit configured for implantation in a body of a subject. An electrode is coupled to the control unit. The control unit is configured to receive programming instructions via the electrode and to drive current into tissue of the subject via the electrode. Other embodiments are also described.

16 Claims, 1 Drawing Sheet

IMPLANTABLE PULSE GENERATOR PROGRAMMING VIA ELECTRODES

FIELD OF THE INVENTION

The present invention generally relates to implantable medical apparatus. Specifically, the present invention relates to methods and apparatus for programming implantable pulse generators.

BACKGROUND OF THE INVENTION

Implantable pulse generators (IPGs) are used extensively in many diverse medical applications. IPGs are often implanted as artificial cardiac pacemakers, stimulating the heart to contract at regular intervals. Other common applications include control of gastric function, and neurostimulation for treating neurological conditions.

U.S. Pat. No. 6,070,103 to Ogden, which is incorporated herein by reference, describes a connector apparatus system and method for providing a direct electrical connection to an implanted medical device for recharging batteries, reprogramming memory, or accessing data. The apparatus consists of a needle-like male connector in conjunction with an implantable female connector that is attached to the implanted medical device and contains a self-resealing elastomeric septum entry port. The female connector comprises a receptacle chamber that is densely packed with a plurality of randomly intertwining, thin, flexible, and conductive metal fibers. External battery charging equipment can be connected to the implanted medical device's internal battery with the connector apparatus system. The required circuit path for recharging can be completed by the use of two single polarity connector pairs, one single polarity connector pair in conjunction with a grounding plate, or one bipolar connector pair. For the bipolar embodiment of the connector, the male portion has two conductors separated by a sleeve of insulating film while the female portion has two stacked cavities, each with separate sealing septums. A multi-polar embodiment of the connector can be used to interface with the implanted device for functions requiring multiple connections.

U.S. Pat. No. 7,167,755 to Seeberger et al., which is incorporated herein by reference, describes a method of operating a medical device comprising updating a regulatory approval status stored in at least one of the medical device or a second device operable to communicate with the medical device, and enabling or disabling the at least one function in the medical device based on the regulatory approval status. The regulatory approval status corresponds to at least one function performable by the medical device.

U.S. Pat. No. 7,069,552 to Lindberg et al., which is incorporated herein by reference, describes a method for providing software to an implantable medical device system, including an implanted medical device and a presentation unit in communication with each other, in which a most current version of software for operating one or more of these system units is stored at a server which is remote from the implanted medical device system. Upon each start-up of the presentation unit, a communication link is established between the server and the presentation unit, and information is provided from the presentation unit to the server identifying the software which is respectively currently stored in one or more of the system units. The server is described as being capable of determining whether the currently stored software in the system units requires an update and, if so, downloading the software version stored at the server to any of the system units which is/are in need of updated software.

U.S. Pat. No. 5,792,203 to Schroeppel, which is incorporated herein by reference, describes an implantable medical device, such as a pacemaker, for electrically stimulating the heart to beat. It includes two or more node logic units connected by communication paths over which signals between nodes are conducted. Each node can provide pacing energy to an electrode and amplify electrical signals from the electrode. In response to detecting an electrical event from the electrode or pacing an electrode, each node generates a sense signal or a pace signal. The sense and pace signals from each node can be transmitted to all other nodes with or without a time delay. The time delays between nodes are provided by delay modules controlled by a processor. As such, the implantable medical device is described as being capable of being configured to provide a variety of pacemaker therapies.

The following patents and patent applications, which are incorporated herein by reference, may be of interest:

US Patent Application Publication 2006/0287692 to Hall et al.
US Patent Application Publication 2006/0129205 to Boveja et al.
U.S. Pat. No. 5,843,138 to Evers et al.
U.S. Pat. No. 6,363,282 to Nichols et al.

The following articles, which are incorporated herein by reference, may be of interest:

Arabi K et al., "Implantable multiprogrammable microstimulator dedicated to bladder control," Med Biol Eng Comput. 1996 January; 34(1):9-12

Thakor N V, "TA universal program for fully programmable pacemakers," Comput Biol Med. 1983; 13(4):271-9

Dassen W R et al., "PACTOT: a reprogrammable software pacing system," Pacing Clin Electrophysiol. 1985 July; 8(4):574-8

SUMMARY OF THE INVENTION

In some embodiments of the present invention an implantable pulse generator (IPG) comprising electrodes is programmed using the electrodes. The IPG is then implanted into the body of a subject, and the same electrodes are used for driving current into tissue of the subject or sensing electrical activity of tissue of the subject. In some embodiments the IPG drives current via the electrodes toward the heart, gastrointestinal tract, or a nerve of the subject. Alternatively or additionally, the IPG drives current toward another tissue of the subject, and/or senses electrical activity of tissue of the subject.

There is therefore provided, in accordance with an embodiment of the invention, apparatus, including:

a control unit configured for implantation in a body of a subject; and an electrode coupled to the control unit, the control unit being configured to receive programming instructions via the electrode and to drive current into tissue of the subject via the electrode.

In an embodiment, the electrode includes a plurality of electrodes, and the control unit is configured to receive the programming instructions via the plurality of electrodes, and to drive the current into the tissue of the subject via the plurality of electrodes.

In an embodiment, the control unit is configured to drive the current into a heart of the subject.

In an embodiment, the control unit is configured to drive the current into a gastrointestinal tract of the subject.

In an embodiment, the control unit is configured to be switched from an off-mode to an on-mode via the electrode.

There is further provided, in accordance with an embodiment of the invention, apparatus, including:

a control unit configured for implantation in a body of a subject; and an electrode coupled to the control unit, the control unit being configured to receive programming instructions via the electrode and to receive sensing data from the body of the subject via the electrode.

In an embodiment, the electrode includes a plurality of electrodes, and the control unit is configured to receive the programming instructions via the plurality of electrodes, and to receive the sensing data from the body of the subject via the plurality of electrodes.

In an embodiment, the control unit is configured to receive the sensing data from a heart of the subject.

In an embodiment, the control unit is configured to receive the sensing data from a gastrointestinal tract of the subject.

In an embodiment, the control unit is configured to be switched from an off-mode to an on-mode via the electrode.

There is yet further provided, in accordance with an embodiment of the invention, apparatus, including:

a control unit configured for implantation in a body of a subject; and an electrode coupled to the control unit, the control unit being configured to be switched from an off-mode to an on-mode via the electrode, and to drive current into tissue of the subject via the electrode.

There is still further provided, in accordance with an embodiment of the invention, a method, including:

coupling an implantable control unit to a programming unit, via an electrode coupled to the control unit, the electrode being configured to drive current into tissue of a subject when implanted in the subject, the current being generated by the control unit; and programming the control unit via the electrode.

There is also provided, in accordance with an embodiment of the invention, a method, including:

programming an implantable control unit via an electrode coupled to the control unit;

implanting the control unit and the electrode into a body of a subject; and driving current from the control unit into the subject via the electrode.

In an embodiment, implanting the electrode into the body of the subject includes coupling the electrode to cardiac tissue of the subject.

In an embodiment, implanting the electrode into the body of the subject includes coupling the electrode to a gastrointestinal tract of the subject.

In an embodiment, the method includes switching the implantable control unit from an off-mode to an on-mode via the electrode.

There is additionally provided, in accordance with an embodiment of the invention, a method including:

programming an implantable control unit via an electrode coupled to the control unit;

implanting the control unit and the electrode into a body of a subject; and receiving sensing data from the subject's body via the electrode.

There is still additionally provided, in accordance with an embodiment of the invention, a method including:

switching an implantable control unit from an off-mode to an on-mode via an electrode coupled to the control unit;

implanting the control unit and the electrode into a body of a subject; and driving current from the control unit into the subject via the electrode.

In an embodiment, switching the implantable control unit from the off-mode to the on-mode includes driving a current into the implantable control unit.

The present invention will be more fully understood from the following detailed description of embodiments thereof, taken together with the drawings, in which:

DETAILED DESCRIPTION OF EMBODIMENTS

Figure 1:
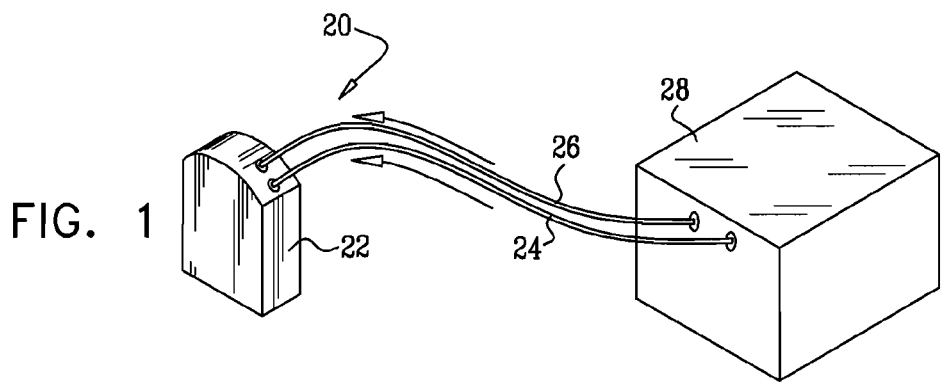
FIG. 1 is a schematic illustration of an IPG coupled to a programming unit, in accordance with an embodiment of the present invention.

Reference is now made to FIG. 1, which is a schematic illustration of an IPG 20 being programmed by a programming unit 28, in accordance with an embodiment of the present invention. The IPG comprises a control unit 22, as well as electrodes 24 and 26 which are coupled to programming unit 28. Programming unit 28 sends programming instructions to control unit 22, via electrodes 24 and 26. In some embodiments, the IPG is a generic IPG, and the programming unit sends instructions to the control unit to function as a specific type of IPG. For example, it may instruct the control unit to function as a cardiac IPG, for stimulating the heart, or as a gastric IPG, for stimulating the stomach. Alternatively, by way of example, the IPG is a cardiac IPG and the programming unit sends instructions to the control unit to modify the pulse pattern of the IPG based on new research, or to optimize the IPG for a given patient.

In some embodiments, control unit 22 of IPG 20 is switched to an on-mode by programming unit 28, via electrodes 24 and 26. Typically, following its manufacture the IPG is stored in an off-mode in which it consumes no power. Shortly before being implanted inside a subject, the IPG is connected to the programming unit via the electrodes. The programming unit drives a current into the IPG causing a switch inside the IPG to switch the control unit into an on-mode. The IPG is then implanted inside the subject's body. This on-mode activation may be practiced even in the absence of programming of the IPG via programming unit 28. Thus, programming unit 28 may simply be used for on-mode activation.

Figure 2:
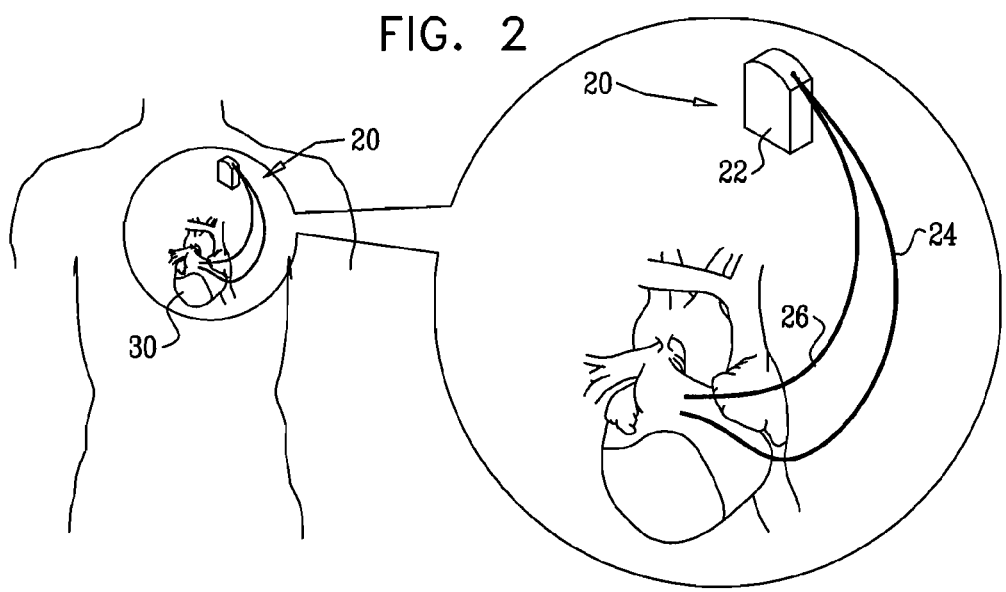
FIG. 2 is a schematic illustration of an IPG coupled to a heart of a subject in accordance with an embodiment of the present invention.

Reference is now made to FIG. 2, which is a schematic illustration of IPG 20 coupled to a heart 30 of a subject, in accordance with an embodiment of the present invention. The IPG typically drives current toward and/or receives sensing data from the heart via electrodes 24 and 26, control unit 22 having received programming instructions via those electrodes.

Figure 3:
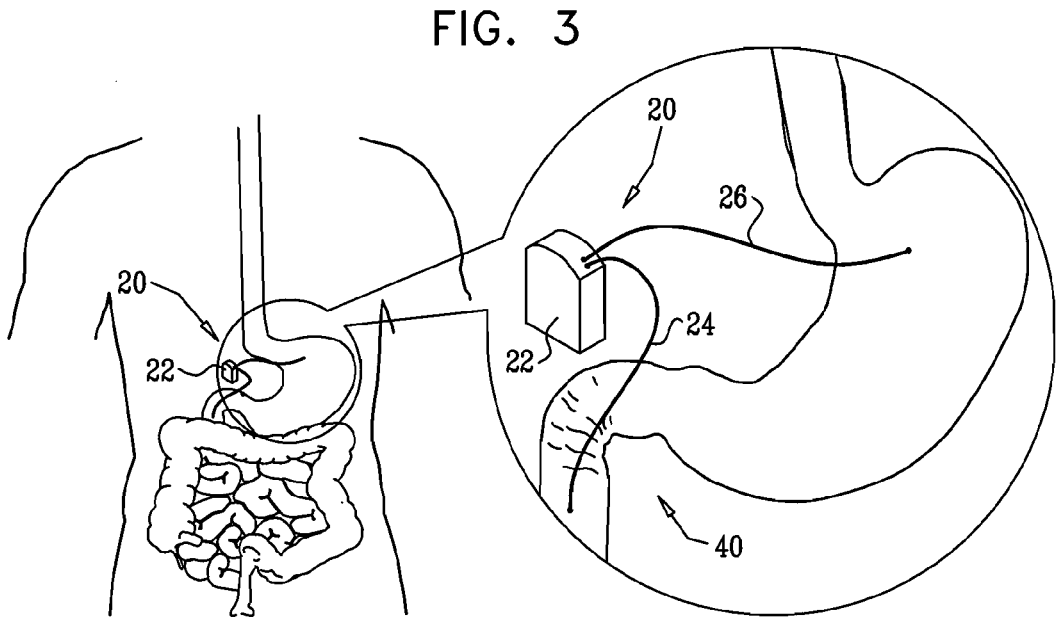
FIG. 3 is a schematic illustration of an IPG coupled to a gastrointestinal tract of a subject in accordance with an embodiment of the present invention.

Reference is now made to FIG. 3, which is a schematic illustration of IPG 20 coupled to one or more sites of a gastrointestinal tract 40 of a subject, in accordance with an embodiment of the present invention. The IPG typically drives current toward and/or receives sensing data from the gastrointestinal tract via electrodes 24 and 26, control unit 22 having received programming instructions via those electrodes.

Although specific IPG's are described hereinabove, the scope of the present invention includes any IPG that is known in the art. For example, IPG 20 may comprise one electrode or a plurality of electrodes. The IPG may be used to drive current toward, and/or receive sensing data from, a subject's nerves, muscles, kidney, liver, pancreas, brain, and/or any other portions of the subject's body.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a programming unit;
   a control unit configured for implantation in a body of a subject; and
   an electrode coupled to the control unit,
   the control unit being configured to:
      be switched from an off-mode to an on-mode via a direct connection between the electrode and the programming unit,
      receive programming instructions via the direct connection between the electrode and the programming unit, and
      drive current into tissue of the subject via the electrode.

2. The apparatus according to claim 1, wherein the electrode comprises a plurality of electrodes, and wherein the control unit is configured to receive the programming instructions via the plurality of electrodes, and to drive the current into the tissue of the subject via the plurality of electrodes.

3. The apparatus according to claim 1, wherein the control unit is configured to drive the current into a heart of the subject.

4. The apparatus according to claim 1, wherein the control unit is configured to drive the current into a gastrointestinal tract of the subject.

5. Apparatus, comprising:
   a programming unit;
   a control unit configured for implantation in a body of a subject; and
   an electrode coupled to the control unit,
   the control unit being configured to:
      be switched from an off-mode to an on-mode via a direct connection between the electrode and the programming unit,
      receive programming instructions via the direct connection between the electrode and the programming unit, and
      receive sensing data from the body of the subject via the electrode.

6. The apparatus according to claim 5, wherein the electrode comprises a plurality of electrodes, and wherein the control unit is configured to receive the programming instructions via the plurality of electrodes, and to receive the sensing data from the body of the subject via the plurality of electrodes.

7. The apparatus according to claim 5, wherein the control unit is configured to receive the sensing data from a heart of the subject.

8. The apparatus according to claim 5, wherein the control unit is configured to receive the sensing data from a gastrointestinal tract of the subject.

9. Apparatus, comprising:
   a programming unit;
   a control unit configured for implantation in a body of a subject; and
   an electrode coupled to the control unit,
   the control unit being configured to
      be switched from an off-mode to an on-mode via a direct connection between the electrode and the programming unit, and
      drive current into tissue of the subject via the electrode.

10. A method, comprising:
    coupling an implantable control unit to a programming unit, via a direct connection between the programming unit and an electrode coupled to the control unit, the electrode being configured to drive current into tissue of a subject when implanted in the subject, the current being generated by the control unit; and
    via the direct connection between the electrode and the control unit:
       switching the control unit from an off-mode to an on-mode; and
       programming the control unit.

11. A method, comprising:
    programming an implantable control unit and switching the control unit from an off-mode to an on-mode via a direct connection between a programming unit and an electrode coupled to the control unit;
    implanting the control unit and the electrode into a body of a subject; and
    driving current from the control unit into the subject via the electrode.

12. The method according to claim 11, wherein implanting the electrode into the body of the subject comprises coupling the electrode to cardiac tissue of the subject.

13. The method according to claim 11, wherein implanting the electrode into the body of the subject comprises coupling the electrode to a gastrointestinal tract of the subject.

14. A method, comprising:
    programming an implantable control unit and switching the control unit from an off-mode to an on-mode via a direct connection between a programming unit and an electrode coupled to the control unit;
    implanting the control unit and the electrode into a body of a subject; and
    receiving sensing data from the subject's body via the electrode.

15. A method comprising:
    switching an implantable control unit from an off-mode to an on-mode via a direct connection between a programming unit and an electrode coupled to the control unit;
    implanting the control unit and the electrode into a body of a subject; and
    driving current from the control unit into the subject via the electrode.

16. The method according to claim 15, wherein switching the implantable control unit from the off-mode to the on-mode comprises driving a current into the implantable control unit.

* * * * *